United States Patent
Yee et al.

(10) Patent No.: US 7,270,673 B2
(45) Date of Patent: Sep. 18, 2007

(54) MICROSURGICAL BALLOON WITH PROTECTIVE REINFORCEMENT

(75) Inventors: Carl Yee, San Diego, CA (US); Ricardo Roman, San Diego, CA (US); Brandon Schwab, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 505 days.

(21) Appl. No.: 10/750,541

(22) Filed: Dec. 31, 2003

(65) Prior Publication Data

US 2005/0149082 A1 Jul. 7, 2005

(51) Int. Cl.
*A61B 17/22* (2006.01)
(52) U.S. Cl. .................................... 606/159
(58) Field of Classification Search ............ 606/159, 606/194, 192, 167, 170, 191
See application file for complete search history.

(56) References Cited

U.S. PATENT DOCUMENTS

| | | | |
|---|---|---|---|
| 4,273,128 A * | 6/1981 | Lary | ............... 606/159 |
| 4,456,000 A | 6/1984 | Schjeldahl et al. | |
| 4,723,549 A | 2/1988 | Wholey et al. | |
| 4,738,666 A | 4/1988 | Fuqua | |
| 4,781,186 A | 11/1988 | Simpson et al. | |
| 4,793,348 A | 12/1988 | Palmaz | |
| 4,867,157 A | 9/1989 | McGurk-Burleson et al. | |
| 4,887,613 A | 12/1989 | Farr et al. | |
| 4,896,669 A | 1/1990 | Bhate et al. | |
| 4,909,781 A | 3/1990 | Husted | |
| 4,986,807 A | 1/1991 | Farr | |
| 5,030,201 A | 7/1991 | Palestrant | |
| 5,047,040 A | 9/1991 | Simpson et al. | |
| 5,053,044 A | 10/1991 | Mueller et al. | |
| 5,074,871 A | 12/1991 | Groshong | |
| 5,078,725 A | 1/1992 | Enderle et al. | |
| 5,102,390 A | 4/1992 | Crittenden et al. | |
| 5,152,773 A | 10/1992 | Redha | |
| 5,156,610 A | 10/1992 | Reger | |
| 5,176,693 A | 1/1993 | Pannek, Jr. | |
| 5,178,625 A | 1/1993 | Groshong | |
| 5,180,368 A | 1/1993 | Garrison | |
| 5,192,291 A | 3/1993 | Pannek, Jr. | |
| 5,196,024 A * | 3/1993 | Barath | ............... 606/159 |
| 5,209,799 A | 5/1993 | Vigil | |
| 5,224,945 A | 7/1993 | Pannek, Jr. | |
| 5,226,909 A | 7/1993 | Evans et al. | |
| 5,250,059 A | 10/1993 | Andreas et al. | |

(Continued)

*Primary Examiner*—(Jackie) Tan-Uyen Ho
*Assistant Examiner*—Pavitra Kotini
(74) *Attorney, Agent, or Firm*—Vidas, Arrett & Steinkraus, P.A.

(57) ABSTRACT

A microsurgical balloon, with at least one incising component mounted to the surface of the balloon, includes a protective pad to prevent the outer surface of the incising component from coming into contact with and damaging the balloon surface. In particular, the protective pad is positioned on the outer surface of the balloon substantially parallel to and juxtaposed with the incising component. When the balloon is in a deflated configuration, either for insertion into the vasculature system or removal from the patient, the protective pad engages the outer surface of the incising component thereby protecting the balloon from being punctured or damaged by the incising component. The protective pad may be bonded to the outer surface of the balloon, or it may be an integral part of a homogeneous balloon structure.

22 Claims, 5 Drawing Sheets

U.S. PATENT DOCUMENTS

| | | | |
|---|---|---|---|
| 5,320,634 A * | 6/1994 | Vigil et al. | 606/159 |
| 5,336,234 A * | 8/1994 | Vigil et al. | 606/159 |
| 5,372,601 A | 12/1994 | Lary | |
| 5,417,703 A | 5/1995 | Brown et al. | |
| 5,441,510 A | 8/1995 | Simpson et al. | |
| 5,478,319 A * | 12/1995 | Campbell et al. | 604/103.08 |
| 5,507,760 A | 4/1996 | Wynne et al. | |
| 5,507,761 A | 4/1996 | Duer | |
| 5,522,825 A | 6/1996 | Kropf et al. | |
| 5,556,405 A * | 9/1996 | Lary | 606/159 |
| 5,556,408 A * | 9/1996 | Farhat | 606/180 |
| 5,569,227 A | 10/1996 | Evan et al. | |
| 5,616,149 A * | 4/1997 | Barath | 606/159 |
| 5,643,296 A | 7/1997 | Hundertmark et al. | |
| 5,728,123 A | 3/1998 | Lemelson et al. | |
| 5,766,203 A * | 6/1998 | Imran et al. | 623/1.11 |
| 5,792,158 A | 8/1998 | Lary | |
| 5,797,935 A * | 8/1998 | Barath | 606/159 |
| 5,800,450 A | 9/1998 | Lary et al. | |
| 6,013,055 A * | 1/2000 | Bampos et al. | 604/103.07 |
| 6,117,153 A | 9/2000 | Lary et al. | |
| 6,213,957 B1 | 4/2001 | Milliman et al. | |
| 6,258,108 B1 * | 7/2001 | Lary | 606/159 |
| 6,306,151 B1 * | 10/2001 | Lary | 606/159 |
| 6,632,231 B2 * | 10/2003 | Radisch, Jr. | 606/159 |
| 7,008,438 B2 * | 3/2006 | O'Brien | 606/194 |
| 2002/0010489 A1 | 1/2002 | Grayzel et al. | |
| 2005/0119678 A1 * | 6/2005 | O'Brien et al. | 606/159 |
| 2005/0137615 A1 * | 6/2005 | Mapes et al. | 606/159 |
| 2005/0137616 A1 * | 6/2005 | Vigil | 606/170 |

\* cited by examiner

MICROSURGICAL BALLOON WITH PROTECTIVE REINFORCEMENT

FIELD OF THE INVENTION

The present invention pertains generally to interventional medical devices. More particularly, the present invention pertains to microsurgical balloons that are used to insert incising components into the vasculature system of a patient. The present invention is particularly, but not exclusively, useful as a device and method for protecting the surface of the microsurgical balloon from damage or puncture caused by the balloon outer surface coming into contact with the incising component.

BACKGROUND OF THE INVENTION

Angioplasty is a well known technique that is commonly used in the treatment of vasculature diseases. An integral part of an angioplasty procedure is the insertion of an inflatable balloon on a catheter into the vasculature of a patient to position the balloon in a vessel at the site of a stenosis. The balloon is then inflated to dilate the stenosis.

A recent innovation in angioplasty procedures involves ablation of a stenosis by an inflated balloon with an incising component mounted on the outer surface of the balloon. Typically the so-called "cutting balloon" will have a plurality of atherotomes (blades) mounted on its outer surface. Once the "cutting balloon" is inflated inside the vessel, the blades create small incisions in the lesion which facilitate dilation of the stenosis and reduce barotrauma. Such a "cutting balloon" is disclosed and claimed in U.S. Pat. No. 5,797,935 which issued to Barath for an invention entitled "Balloon Activated Force Concentrators for Incising Stenotic Segments" and which is assigned to the same assignee as the present invention. While the "cutting balloon" is one example of an interventional medical device that has been developed for performing certain in situ procedures, it is possible for other external components to be mounted on a catheter balloon for therapeutic or diagnostics purposes.

Regardless of the specific incising component that may be mounted on the balloon, a recurring problem is damage that may happen to the balloon during insertion of the catheter or after the balloon inflation and deflation sequence. Prior to insertion, the balloon is typically folded into a so-called "taco shape" or "spiral fold" configuration to reduce its overall profile. Typically, the balloon will come from the manufacturer in this folded configuration. An incising component mounted on the surface of the balloon may, however, prevent the balloon from being folded into its most compact configuration, and may damage the balloon. In addition, damage may occur as the balloon is being maneuvered through the vasculature of a patient. Despite careful manipulation of the catheter through the vasculature system, balloon material may be pushed against the incising surface, damaging the balloon and causing an unwanted rupture.

Yet another opportunity for damage occurs after the balloon has been used for its intended purpose, and is subsequently deflated and withdrawn from the vessel. After deflation, the balloon again collapses inwardly toward its center, for example into a modified "X" configuration. When blades or other incising components are mounted on the balloon, to be located between the legs of the "X", the balloon is particularly vulnerable to damage. Specifically, damage can occur in this configuration if the balloon material is pushed against the incising component during passage through tortuous anatomy or during a twisting of the catheter.

In addition to the problems discussed above, balloon material may have a tendency to fold back on itself, along the axis of the balloon, as the distal end of the balloon contacts the vessel wall or obstructions in the vessel. Importantly, a balloon with an incising component mounted on the outer surface will be more rigid in the area of the incising component. As such, the balloon will tend to fold back, or "kink", in less rigid areas, potentially causing balloon material to fold over and come into contact with the incising component.

In light of the above, it is an object of the present invention to provide a reinforced balloon to protect the areas of the balloon that are likely to be damaged by an incising component. Another object of the present invention is to provide a reinforced balloon that helps to minimize collateral damage to the tissue of a patient. Still another object of the present invention is to provide a balloon that helps to minimize balloon damage resulting from the balloon folding back on itself. Yet another object of the present invention is to provide a reinforced balloon with components mounted on its surface that is easy to use, relatively simple to manufacture, and comparatively cost effective.

SUMMARY OF THE INVENTION

The present invention is directed to an inflatable microsurgical balloon having an incising component mounted on an outer surface of the balloon. A protective pad is positioned on the balloon surface to protect the balloon from being inadvertently cut by the incising component. Specifically, the protective pad is positioned on the outer surface of the balloon such that prior to inflation, and after deflation in the vessel, the protective pad engages the outer cutting surface of the incising component. The balloon is thereby protected from being punctured or otherwise damaged by the incising component. As envisioned for the present invention, an "incising component" may include any component mounted on the outer surface of the balloon with a protrusion capable of cutting, puncturing or otherwise damaging the balloon.

In detail, the balloon is an elongated, inflatable balloon that defines a longitudinal axis. When fully inflated, the surface of the balloon is distanced radially from the longitudinal axis. For the present invention, at least one incising component is mounted on the outer surface of the balloon. Juxtaposed with, and parallel to, the incising component is a protective pad. The protective pad may be manufactured from a substantially impenetrable material or from a semipenetrable material. Importantly, the protective pad may have an extended length, greater than the length of the incising component, to provide additional stiffness to the balloon in the longitudinal direction. The protective pad is positioned to engage the outer cutting surface of the incising component when the balloon is folded prior to insertion into the patient, or when the balloon is deflated after use in the vasculature. In an alternate embodiment of the present invention, a protective pad may also be positioned at one or both ends of the incising component, to engage the incising component in those instances when the balloon "kinks" or folds back along itself in a longitudinal direction.

In the preferred embodiment of the present invention, the incising component comprises an elongated blade with an outer cutting surface running the length of the blade. Further, the protective pad is a single, continuous pad mounted on the outer surface of the balloon, juxtaposed with and parallel to the elongated blade. In an alternate embodiment of the present invention, the protective pad comprises a plurality of axially aligned sections, wherein adjacent sections are separated by a depression. In yet another embodiment, the pad is a localized area of thicker balloon material, manufactured as an integral part of a homogeneous balloon structure.

With regard to the incising component, it is within the contemplation of the present invention that a plurality of incising components may be mounted axially, parallel to the longitudinal axis of the balloon. Further, a plurality of incising components may be axially aligned but azimuthally separated on the balloon. In yet another embodiment of the present invention, the incising component comprises an elongated blade and a base, with the base mounted on the outer surface of the balloon, and the blade mounted on the base. When the balloon is folded or deflated, the protective pad may engage either the base or the blade, thereby preventing the elongated blade from coming into contact with the balloon outer surface. The base may be shaped to increase the stiffness of the balloon in the longitudinal direction, thereby minimizing the possibility that the balloon will "kink" or fold back along itself. In addition, the base may be manufactured with one or more longitudinal stiffeners molded into the base. It is further contemplated by the present invention that the incising component may include an elongated tab at the proximal and distal end of the blade to increase the longitudinal stiffness of the balloon. The tab is an axial extension of the blade, and it is bonded to the outer surface of the base.

Prior to use, the inflatable balloon may be delivered by the manufacturer in a deflated, "folded" configuration. When folded, balloon material is wrapped circumferentially around the axis defined by the balloon. As contemplated by the present invention, when the balloon is folded, the protective pad engages the cutting surface of the incising component. This engagement effectively prevents the cutting surface of the incising component from coming into contact with, and damaging, the outer surface of the balloon.

In operation, the folded balloon is inserted and advanced into the vasculature of a patient to perform a vessel dilation procedure. The increased longitudinal stiffness of the balloon helps to prevent "kinking" during insertion and removal, as the balloon strikes the vasculature wall or other obstructions. Once the balloon is properly positioned, a fluid source is used to inflate the balloon. This inflation then forces the incising component into the vessel wall of the patient to assist in the dilation of the vessel. After the dilation has been completed, the balloon is then deflated for removal from the vasculature system. When deflated, the balloon will collapse inwardly toward its longitudinal axis, returning the balloon to a modified "folded" configuration. As the balloon deflates, the protective pad again engages the cutting surface of the incising component to prevent an unwanted and inadvertent rupture of the balloon surface by the incising component. In this configuration, the incising component is also prevented from damaging the vessel wall of the patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
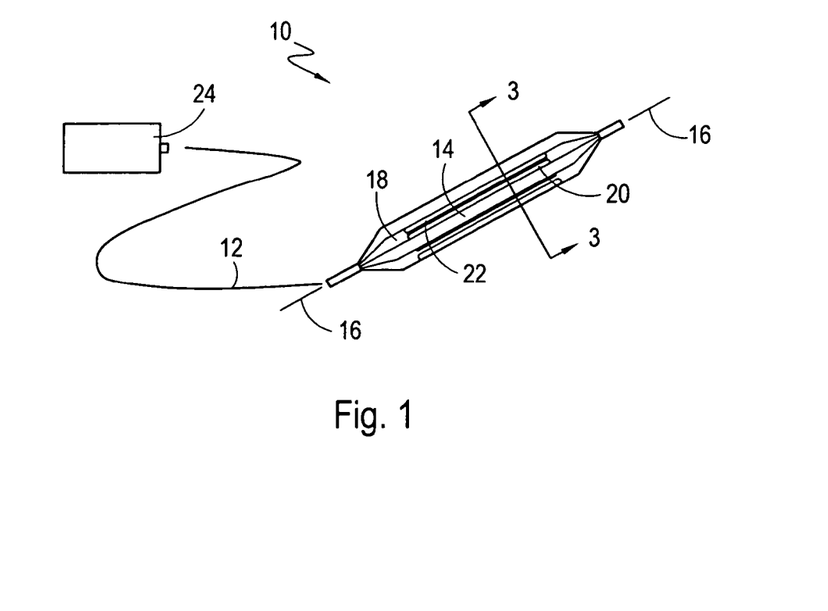
FIG. 1 is a perspective view of an inflatable balloon catheter system incorporating an incising component and a protective pad, in accordance with the present invention.

A system in accordance with the present invention is shown in FIG. 1 and is generally designated 10. As shown, the system 10 has a catheter 12, and an inflatable microsurgical balloon 14 that is attached to the catheter 12. The balloon 14 is an elongated, inflatable balloon 14 that defines a longitudinal axis 16. Mounted on the outer surface 18 of the balloon 14 is an incising component 20. As shown in FIG. 1, positioned substantially parallel to and juxtaposed with the incising component 20 is a protective pad 22. In the preferred embodiment of the present invention, the incising component 20 and the protective pad 22 are mounted on the outer surface 18 of the balloon 14 in a manner well known in the pertinent art, such as by adhesive bonding. The protective pad 22 may be manufactured from a substantially impenetrable or a semi-penetrable material. As further shown in FIG. 1, the system 10 includes an extracorporeal fluid pump 24 that is connected to the catheter 12. The extracorporeal fluid pump 24 is used to selectively inflate and deflate the balloon 14 by introducing fluid into, or in the alternative extracting fluid from, the system 10. In detail, the structure of the protective pad 22 and the incising component 20 will be best appreciated by referring to FIG. 2.

Figure 2:
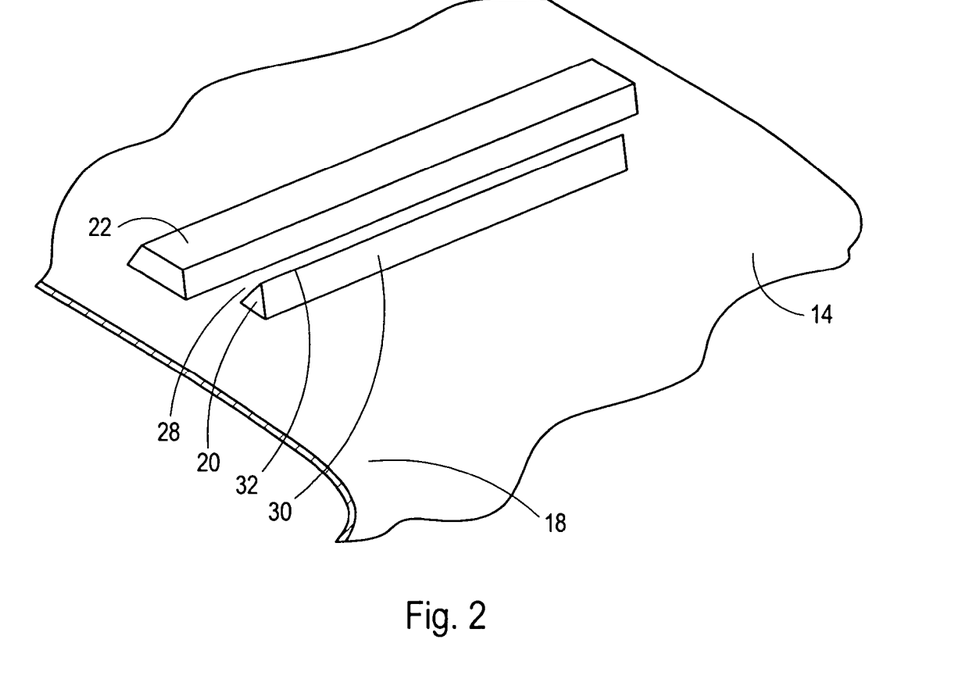
FIG. 2 is a perspective view of a protective pad and incising component mounted on the outer surface of a balloon.

As shown in FIG. 2, the protective pad 22 and the incising component 20 are mounted on the outer surface 18 of the balloon 14. In an alternate embodiment of the present invention, the incising component 20 may be mounted on a base 26 (not shown in FIG. 2), which in turn is mounted on the outer surface 18 of the balloon 14. The incising component 20 is mounted on the balloon 14 with a gap 28 between the incising component 20 and the protective pad 22. Importantly, the width of the gap 28 must be sufficiently small to ensure the incising component 20, as it rotates toward the protective pad 22, engages the protective pad 22, and does and not engage the surface 18 of the balloon 14. In the preferred embodiment of the present invention, the incising component 20 comprises a blade 30 with an outer cutting surface 32 running the length of the elongated blade 30. In addition, the protective pad 22 is a single, continuous pad mounted parallel to, and juxtaposed with, the incising component 20. Variations in the relative position of the protective pad 22 and the incising component 20 can best be appreciated by referring to the cross-sectional views in FIGS. 3A-3E.

Figure 3A:
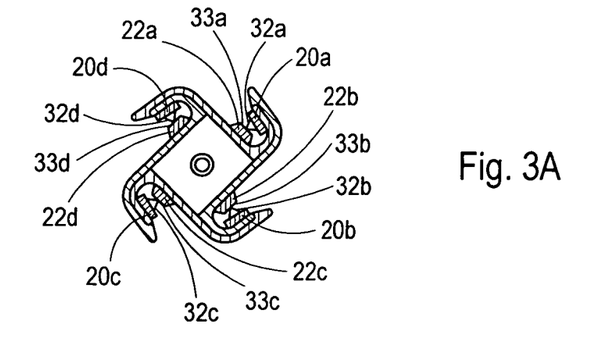
FIG. 3A is a cross-sectional view of a balloon in a "folded" configuration, as would be seen along the line 3-3 in FIG. 1, when the balloon is deflated prior to use.
Figure 3B:
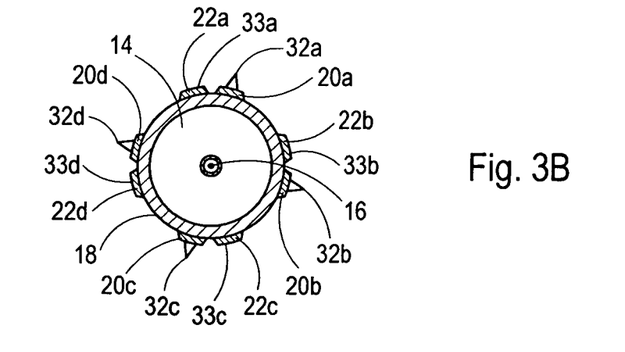
FIG. 3B is a cross-sectional view of a balloon in its fully inflated configuration, as would be seen along line 3-3 in FIG. 1.
Figure 3C:
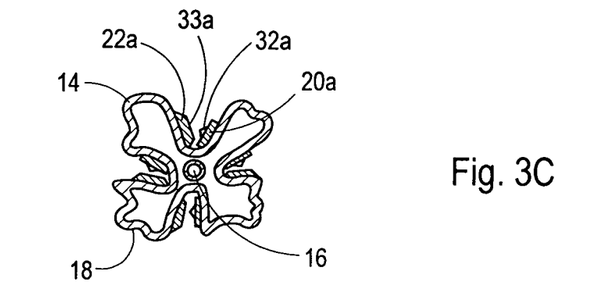
FIG. 3C is a cross-sectional view of a deflated balloon, after use in a patient, as would be seen along the line 3-3 in FIG. 1.

In FIG. 3A, it will be noted that when the balloon 14 is folded prior to insertion into the vasculature of a patient, the cutting surfaces 32a, 32b, 32c, and 32d of the incising components 20a, 20b; 20c, and 20d are engaged by the outer surfaces 33a, 33b, 33c, and 33d of the protective pads 22a, 22b, 22c, and 22d. As shown in FIG. 3B, when the balloon 14 is fully inflated, the protective pads 22a-d and the incising components 20a-d are distanced radially from the axis 16. The outer surfaces 33a-d of the protective pads 22a-d, and the cutting surfaces 32a-d of the incising components 20a-d, are oriented substantially normal to the outer surface 18 of the balloon 14. Further, as is shown in FIG. 3C, when the balloon 14 is deflated after use, the balloon 14 will collapse inwardly towards the axis 16. As the balloon 14 deflates, it will return to a modified version of the pre-insertion, folded configuration. Specifically, the protective pad 22a falls inwardly towards the longitudinal axis 16 and rotates towards the incising component 20a. Likewise, the incising component 20a falls inwardly and rotates toward the protective pad 22a. Consequently, the outer surface 33a of the protective pad 22a engages the cutting surface 32a of the incising component 20a. In a like manner, the remaining protective pads 22b-d and incising components 20b-d fall, rotate and engage.

Figure 3D:
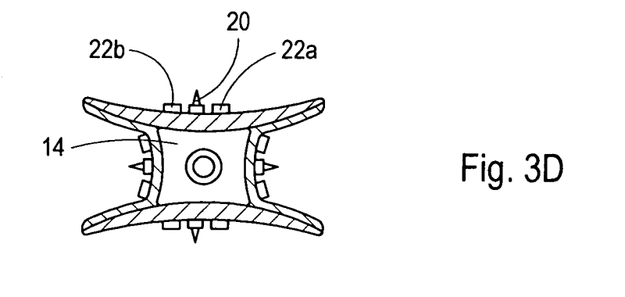
FIG. 3D is a cross-sectional view of a deflated balloon having a protective pad on either side of an incising component.

In an alternate embodiment of the present invention, as shown in FIG. 3D, two protective pads, of which pads 22a and 22b are exemplary, are mounted juxtaposed with, and parallel to, an incising component 20. In this configuration the incising component 20 engages a protective pad 22a and 22b, regardless of the direction of rotation of the incising component 20.

Figure 3E:
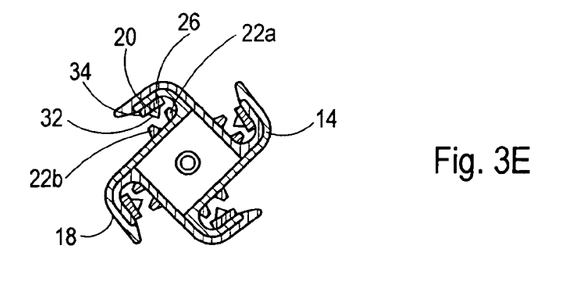
FIG. 3E is a cross-sectional view of an alternate embodiment of a balloon in a "folded" configuration, as would be seen along the line 3-3 in FIG. 1, when the balloon is deflated prior to use.

Referring now to FIG. 3E it can be seen that the incising component 20 comprises a base 26 with an outer surface 34, and an elongated blade 30 with an outer cutting surface 32. As contemplated by the present invention, two protective pads 22a and 22b are positioned to engage the outer surface 34 of the base 26. When the protective pads 22a and 22b engage the base 26, the cutting surface 32 of the incising component 20 does not contact the outer surface 18 of the balloon 14.

Figure 4A:
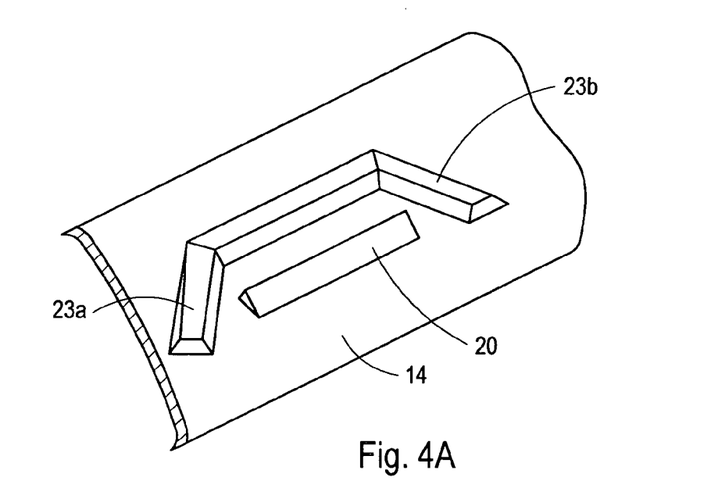
FIG. 4A is a perspective view of an alternate embodiment of a protective pad with extensions positioned at either end of an incising component.
Figure 4B:
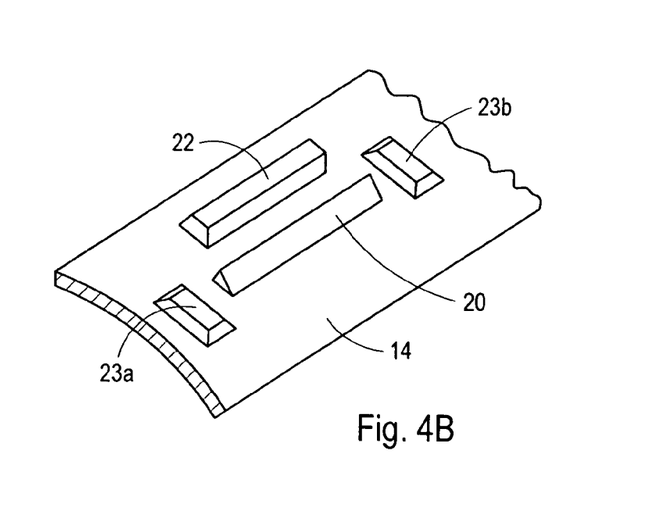
FIG. 4B is a perspective view of an alternate embodiment of a protective pad positioned at either end of an incising component.

With regard to the protective pad 22, as shown in FIGS. 3A-3E, the pad 22 may be bonded to the outer surface 18 of the balloon 14. In an alternate embodiment of the present invention, the protective pad 22 may be a localized area of thicker, or reinforced, balloon 14 material, manufactured as an integral part of a homogeneous balloon 14 structure. In addition, as shown in FIGS. 4A and 4B, protective pads, of which 23a and 23b are exemplary, may be positioned to engage the incising component 20 when the balloon 14 "kinks" or folds back on itself.

Figure 5:
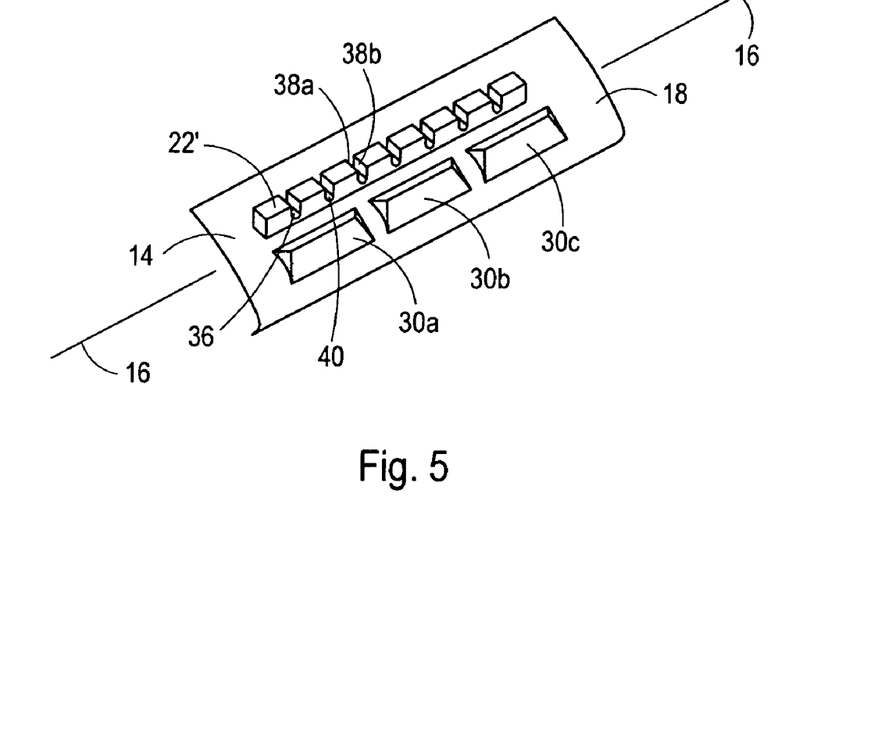
FIG. 5 is a perspective view of an alternate embodiment of a protective pad and an incising component.

Considering now FIG. 5, in yet another embodiment of the present invention, the protective pad 22' comprises a plurality of axially aligned sections, wherein adjacent sections are separated by a depression 36. The depression 36 has a side wall 38a and a side wall 38b that extend vertically at an angle from the outer surface 18 of the balloon 14. In addition, the depression 36 has a floor 40. The floor 40 is substantially parallel to, and located radially outward from, the outer surface 18 of the balloon 14. The floor 40 connects adjacent sections of the pad 22'. Additionally, as shown in FIG. 5, a plurality of elongated blades (e.g. blades 30a, 30b and 30c) are axially oriented and substantially parallel to the axis 16 of the balloon 14. It can be contemplated by referring to FIG. 5 that the system 10, with a protective pad 22', and a plurality of elongated blades 30a-c, will have increased axial flexibility. Increased flexibility in the axial direction, along the length of the balloon 14, provides for greater ease of movement of the catheter 12 through the vasculature system of the patient.

Figure 6:
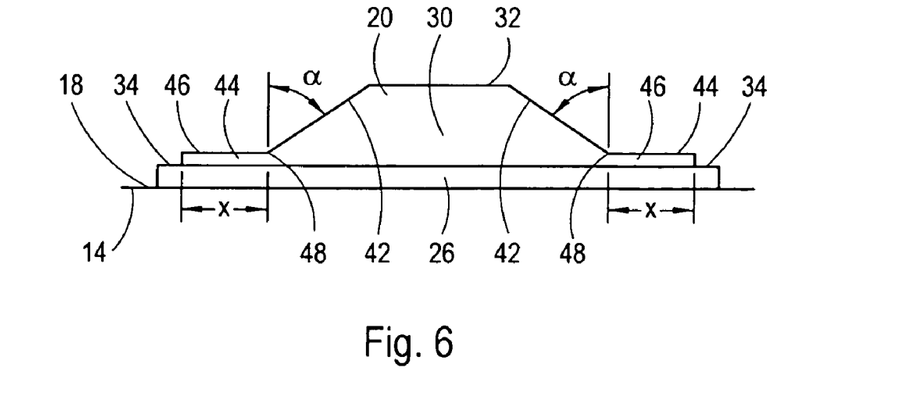
FIG. 6 is a side view of an incising component comprising an elongated blade mounted on a base.

As shown in FIG. 6, the incising component 20 may comprise a base 26 and a blade 30 with an outer cutting surface 32. The base 26 is mounted on the outer surface 18 of the balloon 14, and the blade 30 is mounted to the base 26. Further, as shown in FIG. 6, the blade 30 includes a tapered region 42, and an elongated tab 44 at both the proximal and distal ends of the blade 30. The tapered region 42 of the blade 30 extends from the outer surface 46 of the tab 44 to the outer cutting surface 32 of the blade 30, at an angle "α" measured from a line drawn normal to the outer surface 46 of the tab 44. Referring still to FIG. 6, the tab 44 extends axially from the bottom of the tapered region 48 for an elongated distance "X", thereby providing increased stiffness to the blade-base combination. The tab 44 may be bonded on the outer surface 34 of the base 26.

Figure 7A:
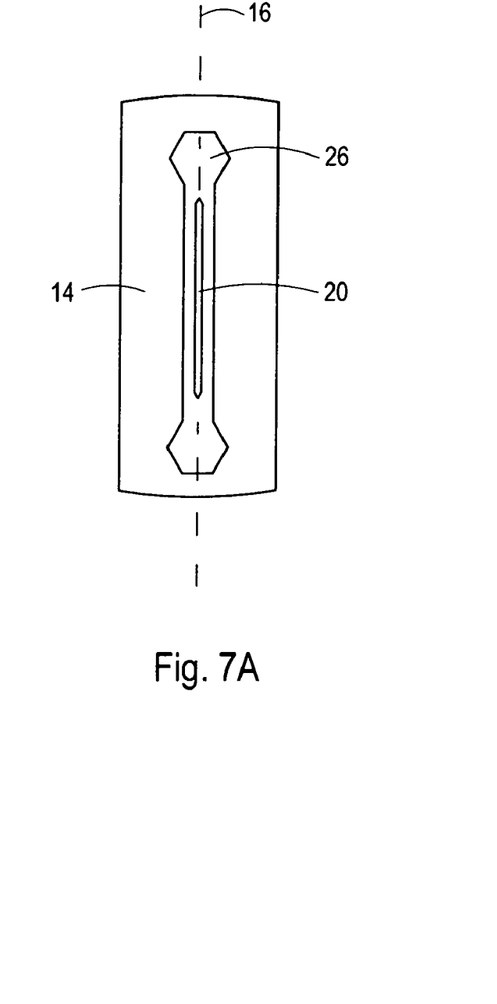
FIG. 7A is a top view of an alternate embodiment of a base mounted to the surface of a balloon.
Figure 7B:
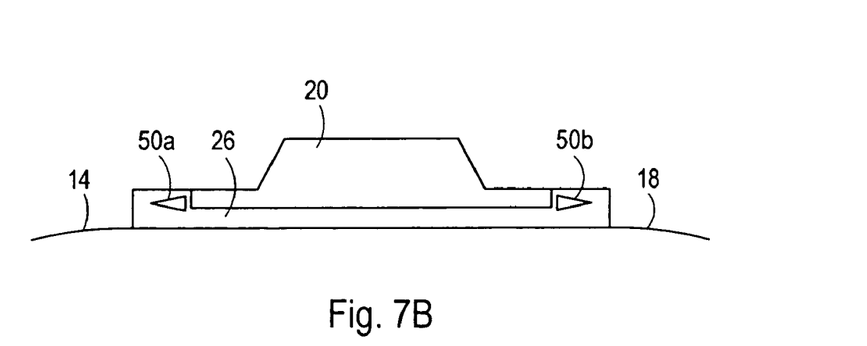
FIG. 7B is a side view of an alternate embodiment of an incising component bonded to a base with two stiffeners.

Referring now to FIGS. 7A and 7B, the base 26 may be shaped to provide the balloon 14 increased longitudinal stiffness. As shown in FIG. 7A, the base 26 has an increased surface area at either end of the base 26. The increased surface area provides the balloon 14, to which the base 26 is bonded, increased stiffness in the longitudinal direction, which is to say along the longitudinal axis 16. In addition, as shown in FIG. 7B, the incising component 20 may be inset into the base 26, thereby providing additional stiffness to the base 26, and hence the balloon 14. Also, as shown in FIG. 7B, the base 26 may be manufactured with a plurality of stiffeners 50a and 50b molded into the interior of the base 26. A shaped base 26, as in FIGS. 7A and B, or a base 26 with added stiffeners 50a and 50b (FIG. 7B), will provide the balloon 14 increased stiffness in the longitudinal direction. The increased stiffness minimizes the possibility that the balloon 14 will "kink", or fold back on itself when contacting structure within the vasculature.

While the particular microsurgical balloon and system as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A microsurgical balloon which comprises: an elongated, inflatable balloon having an outer surface and defining a longitudinal axis, wherein said outer surface of said balloon is distanced radially from said axis when said balloon is in an inflated configuration and said surface is collapsed along said axis when said balloon is in a deflated configuration; at least one incising component positioned on said surface of said balloon for movement therewith; a pad having an outer surface, wherein said pad is positioned on said balloon, completely spaced apart from, substantially parallel to and juxtaposed with said incising component, in the deflated configuration said outer surface of said pad being engaged to the incising component, in the inflated configuration said incising component being removed from engagement with said pad such that said pad does not contact said incising component.

2. A balloon as recited in claim 1 wherein said pad comprises a plurality of axially aligned sections.

3. A balloon as recited in claim 1 wherein said pad is formed on said outer surface of said balloon as a homogeneous structure with said balloon.

4. A balloon as recited in claim 1 wherein said incising component comprises a base and an elongated blade, and further wherein said base is mounted on said outer surface of said balloon, and said elongated blade is mounted on said base.

5. A balloon as recited in claim 4 wherein said pad is located to engage said base when said balloon is in its deflated configuration.

6. A balloon as recited in claim 1 wherein a pad is positioned on either side of said incising component.

7. A balloon as recited in claim 1 wherein said balloon includes a plurality of incising components mounted on said balloon, axially oriented and substantially parallel to said axis of said balloon.

8. A balloon as recited in claim 1 wherein said balloon includes a plurality of incising components mounted azimuthally on said balloon.

9. A balloon as recited in claim 4 wherein said base is formed with a plurality of stiffeners.

10. A system for protecting a balloon in the vasculature of a patient during a vessel dilation procedure, said system comprising: an elongated, inflatable balloon having an outer surface and defining a longitudinal axis, wherein said surface of said balloon is distanced radially from said axis when said balloon is in an inflated configuration and said surface is collapsed along said axis when said balloon is in a deflated configuration; an inflation means for moving the balloon between its deflated configuration and its inflated configuration; an incising means positioned on said outer surface of said balloon for movement therewith for incising the vessel when said balloon is in its inflated configuration; a protective means positioned on said outer surface of said balloon, completely spaced apart from, substantially parallel to and juxtaposed with said incising means, in the deflated configuration said protective means being engaged to the incising means, in the inflated configuration said incising means being removed from engagement with said protective means such that protective means is not in contact with said incising means.

11. A system as recited in claim 10 wherein said protective means comprises a pad, and further wherein said pad comprises a plurality of axially aligned sections.

12. A system as recited in claim 10 wherein said protective means and said balloon are a homogeneous structure.

13. A system as recited in claim 10 wherein said incising means comprises a base and an elongated blade, and further wherein said base is mounted on said outer surface of said balloon, and said elongated blade is mounted on said base.

14. A system as recited in claim 13 wherein said protective means is located to engage said base when said balloon is in its deflated configuration.

15. A system as recited in claim 10 wherein a pad is positioned on either side of said incising component.

16. A system as recited in claim 10 wherein said incising means comprises a plurality of elongated blades mounted on said balloon, axially oriented and substantially parallel to said axis of said balloon.

17. A system as recited in claim 13 wherein said base is formed with a plurality of stiffeners.

18. A method for protecting a balloon in the vasculature of a patient during a vessel dilation procedure which comprises the steps of: providing an elongated, inflatable balloon having an outer surface and defining a longitudinal axis, wherein said surface of said balloon is distanced radially from said axis when said balloon is in an inflated configuration, and said surface is collapsed along said axis when said balloon is in a deflated configuration, with at least one incising component positioned on said surface of said balloon, and at least one pad having an outer surface, wherein said pad is positioned on said balloon, completely spaced apart from, substantially parallel to and juxtaposed with said incising component, and further wherein in the deflated configuration said outer surface of said pad is engaged to the incising component in the inflated configuration said incising component is removed from engagement with said pad such that said pad does not contact said incising component; inserting said balloon in its deflated configuration into the vasculature of a patient; inflating said balloon into its inflated configuration for emplacement of said incising component in said vasculature of said patient; and deflating said balloon to return said balloon substantially to its deflated configuration for removal of said incising component from said vasculature of said patient.

19. A method as recited in claim 18 wherein said pad and said balloon are a homogeneous structure.

20. A method as recited in claim 18 wherein a pad is positioned on either side of said incising component.

21. A method as recited in claim 18 wherein said incising component comprises a base and an elongated blade, and wherein said base is mounted on said outer surface of said balloon, and said elongated blade is mounted on said base.

22. A method as recited in claim 20 wherein said base is formed with a plurality of stiffeners.

* * * * *